US006414151B1

(12) United States Patent
Matson et al.

(10) Patent No.: US 6,414,151 B1
(45) Date of Patent: *Jul. 2, 2002

(54) PROCESS FOR MAKING 1,3-DISUBSTITUTED-4-OXOCYCLIC UREAS

(75) Inventors: Patricia Ann Matson, Poolville; Michael Selden Godlewski, Morris, both of NY (US); Daniel Joseph Quarroz, Baltschieder; Yves Guggisberg, Sierre, both of (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,231

(22) PCT Filed: Apr. 27, 1999

(86) PCT No.: PCT/US99/09092

§ 371 (c)(1),
(2), (4) Date: Oct. 27, 2000

(87) PCT Pub. No.: WO99/55700

PCT Pub. Date: Nov. 4, 1999

(51) Int. Cl.[7] ............................. C07D 405/14
(52) U.S. Cl. ................... 544/370; 548/316.1
(58) Field of Search ........................ 544/370

(56) References Cited

U.S. PATENT DOCUMENTS

| | | | | |
|---|---|---|---|---|
| 3,906,010 A | 9/1975 | Pelosi, Jr. et al. | ....... | 260/347.5 |
| 3,919,231 A | 11/1975 | Pelosi, Jr. et al. | ....... | 260/256.4 |
| 3,946,049 A | 3/1976 | Pelosi, Jr. | ........ | 260/347.2 |
| 4,001,222 A | 1/1977 | White, Jr. | ........ | 260/240 G |
| 4,559,354 A | 12/1985 | Fuhrer et al. | ........ | 514/357 |
| 5,019,651 A | 5/1991 | Kieczykowski | ........ | 562/13 |
| 5,462,940 A | 10/1995 | Yu et al. | ........ | 5414/235.8 |

FOREIGN PATENT DOCUMENTS

| | | |
|---|---|---|
| EP | 0251380 A2 | 7/1988 |
| EP | 0321431 A1 | 6/1989 |
| IN | 159119 | 7/1980 |
| WO | WO 93/04064 | 3/1993 |

OTHER PUBLICATIONS

Krustosikova, A; Kovac, J, et al; Furan Derivatives. XXVII Synthesis and Absorption Spectra of Methyl–2–cyano–3–[5–(X–phenyl)–2–furyl]acrylates, *Chem. Zvesti* 25; vol. 25(2), 142–146, (1971).

Frimm, R, et al; Furan Derivatives XXXI α,β–Unsaturated ketones of the phenylfuran series, *Chem. Zvesti* 27(1) 101–106 (1973).

Frimm, R, et al; Furan Derivatives. XXIII Synthesis and Absorption Spectra of 5–(Nitrophenyl)–2–furaldehyde Derivatives, *Chem. Zvesti* 23, 916–922 (1969).

Somasekhara, S., et al; Derivatives of 5–Substituted Furfuraldehydes, *Current Science*, 37 (21) 1968 pp. 614–616.

Ellis, K.O. et al; Synthesis and Skeletal Muscle Relaxant Activity of Quaternary Ammonium Salts of Dantrolene and Chodanolene, *J of Pharmaceutical Sciences*, vol. 69, No. 3, (327–31) Mar. 1980.

Pong, S.F. et al; 5–Phenyl–2–furamidines; a New Chemical Class of Potential Antidepressants, *Arzneim.–Forsch.* vol. 33(10), pp. 1411–1416, 1983.

Ellis, K., et al; Synthesis and Comparative Skeletal Muscle Relaxant Activity of Some 2,4–Imidazolidinediones and Their Corresponding 5–Hydroxy–2,4–imidazolidnediones, *J of Medicinal Chemistry*, vol. 21, No. 1, pp. 127–133, (1978).

Janda, L., et al, Semisynthetic cephalosporines I. An Improved Synthesis of 5–aryl–2–furancarboxylic acids, *Chem. Zvesti* 38 (4) 507–513 (1984).

Davis, C.S., et al, Synthesis of 5–Phenyl–2–furaldehyde, *J of Heterocycle Chem.*, 4(1), 153–4, Mar. 1967.

Burch, Homer A., et al; Phenylfurans IV: Spasmolytic 3–Diethylamino–2,2–(dimethyl)propyl Esters of 5–Substituted Phenyl–2–furancarboxylic Acids, *J of Pharmaceutical Sciences*, vol. 69, No. 1, Jan. 1980, pp. 107–110.

Wessels, F.L, et al, Synthesis and Skeletal Muscle Relaxant Activity of 3–(Aminoacyl)–1–[[[5–(substituted phenyl)–2–furanyl]methylene]amino]–2,4–imidazolidinediones, *J of Pharmaceutical Sciences*, vol. 70, No. 9, Sep. 1981, pp. 1088–1090.

*Primary Examiner*—Emily Bernhardt
(74) *Attorney, Agent, or Firm*—Richard S. Echler, Sr.; Mary Pat McMahon

(57) ABSTRACT

A process for making 1-[[[5-(4-chlorophenyl)-2-furanyl]methylene]amino]-3-[4-(4-methyl-1-piperizinyl)butyl]-2,4-imidazolidinedione having the formula:

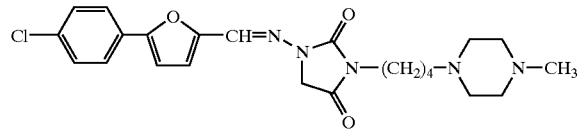

is disclosed. The process circumvents the use of sodium hydride and isolation of reaction intermediates following the initial coupling of the hydantoin intermediate and 4-N-methylpiperizine.

17 Claims, No Drawings

PROCESS FOR MAKING 1,3-DISUBSTITUTED-4-OXOCYCLIC UREAS

FIELD OF THE INVENTION

The present invention relates to chemical processes for making compounds useful in the treatment of various medical disorders; such uses include but are not limited to uses as antifibrillatory and antiarrhythmic agents. The processes of this invention are useful for making 1,3-disubstituted-4-oxocyclic ureas, particularly 1-[[[5-(4-Chlorophenyl)-2-furanyl]methylene]amino]-3-[4-(4-methyl-1-piperazinyl) butyl]-2,4-imidazolidinedione and salts thereof.

BACKGROUND OF THE INVENTION

The present invention relates to a process for making 1,3-disubstituted-4-oxocyclic ureas, particularly 1-[[[5-(4-Chlorophenyl)-2-furanyl]methylene]amino]-3-[4-(4-methyl-1-piperazinyl)butyl]-2,4-imidazolidinedione or salts thereof, where the end product is obtained in pure form and high yield.

1-[[[5-(4-Chlorophenyl)-2-furanyl]methylene]amino]-3-[4-(4-methyl-1-piperazinyl)butyl]-2,4-imidazolidinedione dihydrochloride (Azimilide) is disclosed in U.S. Pat. No. 5,462,940 (1995) to Norwich Eaton Pharmaceuticals, Inc.; said disclosure is incorporated herein by reference. Two general methods are disclosed in U.S. Pat. No. 5,462,940 issued to Yu et al Oct. 31, 1995 for this type of compound. Each describes a series of reactions which involve isolation of three to five intermediate compounds. The disadvantages of both methods are the use of highly flammable and moisture sensitive sodium hydride, potentially explosive DMF/sodium hydride mixtures, excessive solvent volumes, sodium iodide, and several isolation steps. Added disadvantages of one method are: the use of an amine protecting group and the need for a hydrogenation reaction for its removal.

It is apparent from the art that safer, higher yielding, more economical methods of preparing Azimilide would be advantageous. Particularly advantageous would be a reduction in the number of synthetic steps, increased reaction throughput (higher reaction concentrations), removal of a hydrogenation reaction, elimination of an amine protecting group, higher overall yields, ability to process at large scale, and better final product isolations. It has been surprisingly discovered that the disadvantages of the literature syntheses of these compounds may be overcome by carrying out the sequence of reactions with a mild base such as potassium carbonate for alkylation, eliminating the use of sodium iodide to facilitate alkylation of the amine moiety, and using solvents such as methyl sulfoxide (DMSO) and N-methylpyrrolidone (NMP) to allow considerably higher reaction concentrations. increased product yield and purity.

The subject of this patent is a process for making 1,3-disubstituted-4-oxocyclic ureas whereby the 1,3-disubstituted-4-oxocyclic ureas are conveniently synthesized in high yields, without isolation of intermediates, by first alkylating the corresponding 1-substituted-4-oxocyclic urea with a carbon chain containing up to two leaving groups to form an adduct that is used without isolation to alkylate an amine to form a 1,3-disubstituted-4-oxocyclic urea that is finally reacted with an acid to form the desired salt. The present process allows for the preparation of 1,3-disubstituted-4-oxocyclic ureas under reaction conditions that eliminate the need for a hydrogenation step and the use of an amine protecting group. This process allows for improved yields and product purity, higher throughput, and provides additional synthetic simplicity for the preparation of these classes of molecules.

In particular, the preferred processes of the present invention provide a new methodology that is especially suited for the scale-up and manufacture of Azimilide.

SUMMARY OF THE INVENTION

The present invention provides a process for making 1,3-disubstituted-4-oxocyclic ureas of the general formula:

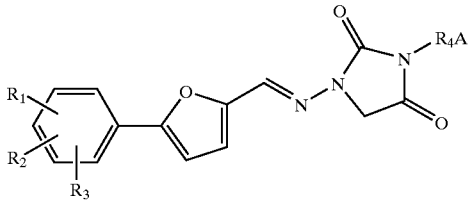

wherein $R_1$, $R_2$, and $R_3$ are independently selected from the group consisting of H, Cl, F, Br, $NH_2$, $NO_2$, COOH, $CH_3SO_2NH$, $SO_3H$, OH, alkoxy, alkyl, alkoxycarbonyl, hydroxyalkyl, carboxyalkyl, and acyloxy;

$R_4$ is selected from the group consisting of a substituted or unsubstituted alkyl, alkenyl, alkynyl, alkylacyl, and heteroalkyl; and A is a substituted or unsubstituted, saturated or unsaturated, straight-chain or branched alkyl or alkenyl amino group comprised of 1–7 carbon atoms; or A is a substituted or unsubstituted, saturated or unsaturated heterocycle having 5, 6, or 7 members containing at least one nitrogen, and $R_4$ is attached to this nitrogen;

wherein said 1,3-disubstituted-4-oxocylic urea is made without isolation of intermediates and comprising the steps:

(Ia) reacting a 1-substituted-4-oxocyclic urea with a carbon chain containing at least two leaving groups in the presence of a mild base and a solvent to form an adduct containing at least one leaving group, and (Ib) condensing the adduct with an amine to form a 1,3-disubstituted-4-oxocyclic urea, and (II) recovering said 1,3-disubstituted-4-oxocyclic urea. This method is particularly preferred for making Azimilide. The 1-subsituted-4-oxocyclic urea used in making Azimilide is 1-[[[5-(4-chlorophenyl)-2-furanyl]methylene]amino]-2,4-imidazolidinedione.

DEFINITIONS AND USAGE OF TERMS

The following is a list of definitions for terms used herein:

As used herein, "acid" means an inorganic or organic acid. An inorganic acid is a mineral acid, such as sulfuric, nitric, hydrochloric, and phosphoric. An organic acid is an organic carboxylic acid, such as formic acid, acetic acid, chloroacetic acid, dichloroacetic acid, propionic acid, benzoic acid, maleic acid, fumaric acid, succinic acid, and tartaric acid.

As used herein, "adduct" means a chemical reaction intermediate or product containing a newly installed functional group.

As used herein, "alkenyl" means a hydrocarbon substituent with one or more double bonds, straight or branched chain, unsubstituted or substituted.

As used herein, "alkoxy" means a substituent having the structure Q—O—, where Q is alkyl or alkenyl.

As used herein, "alkyl" means a saturated hydrocarbon substituent, straight or branched chain, unsubstituted or substituted.

As used herein, "base" means a basic reagent which is added to a reaction mixture to facilitate alkylation of nitrogen using an alkylating agent. Bases include nitrogen bases and inorganic bases such as N,N-diisopropylethylamine, triethylamine, trimethylamine, 4-dimethylaminopyridine, pyridine, sodium hydride, potassium hydride, potassium carbonate, sodium carbonate, potassium bicarbonate, and sodium bicarbonate.

As used herein, "halogen" is a chloro, bromo, fluoro, or iodo atom radical. Bromo, and chloro are preferred halogens.

As used herein, "heterocyclic ring" is a saturated, unsaturated, or aromatic ring radical comprised of carbon atoms and one or more heteroatoms in the ring. Heterocyclic rings are monocyclic or are fused, bridged, or Spiro polycyclic ring systems. Monocyclic rings contain from 3 to 9 atoms, preferably 4 to 7 atoms, and most preferably 5 or 6 atoms. Polycyclic rings contain from 7 to 17 atoms, preferably from 7 to 14 atoms, and most preferably 9 or 10 atoms.

As used herein, "leaving group" means any substituted or unsubstituted alkyl or aryl sulfonate or substituted or unsubstituted alkyl halide. Preferred substituents are halogens.

As used herein, "methylene" is a —CH$_2$— radical.

As used herein, "polar aprotic solvent" is a solvent that possesses the property of high polarity, yet does not have the ability to donate a proton. Preferred polar aprotic solvents include, N,N-dimethylformamide (DMF), N,N-dimethylacetamide (DMAC), N-methylpyrrolidone (NMP), and methyl sulfoxide (DMSO).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, amino, aminoalkyl (e.g. aminomethyl, etc.), cyano, halogen, alkoxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "volumes" refers to liters of indicated solvent per kilogram of starting material.

DETAILED DESCRIPTION OF THE INVENTION

The present invention relates to processes for the manufacture of 1,3-disubstituted-4-oxoeyclic ureas, including but not limited to Azimilide and other pharmaceutically acceptable salts thereof, which can be obtained in high yields, high product purity, high throughput, and with synthetic simplicity. The invention involves a sequential procedure of reacting a 1-substituted-4-oxocyclic urea with a carbon chain reagent containing two leaving groups in a polar aprotic solvent, in the presence of a mild base, reacting further with an amine, precipitating salts with a co-solvent, filtering, and finally adding an acid and recovering 1,3-disubstituted-4-oxocyclic urea or other salts thereof.

The first alkylation takes place at temperatures from 40° to 120° C., preferably at about 60° to 75° C. The base which can be used is selected from those which have easily filterable or otherwise removable salts. Specifically, preferred bases include N,N-diisopropylethylamine, triethylamine, trimethylamine, 4-dimethylaminopyridine, pyridine, sodium hydride, potassium hydride, potassium carbonate, sodium carbonate, potassium bicarbonate, and sodium bicarbonate. The more preferred bases are potassium carbonate, sodium carbonate, potassium bicarbonate, and sodium bicarbonate. The most preferred base is potassium carbonate, generally 0.8 to 4.0 equivalents, preferably 1.2 to 2 equivalents per mole of imidazolidinedione. Preferred carbon chain reagents are selected from the group containing halogen groups, including but not limited to 1-bromo-4-chlorobutane, 1,4-dichloro- or 1,4-dibromobutane; more preferred is 1-bromo-4-chlorobutane. Those skilled in the art will recognize that butylalcohols, butylsulfonylates and tetrahydrofurane are also used as carbon chain reagents. Generally 0.8 to 2.5 equivalents, preferably 1 to 1.2 equivalents are used per mole of imidazolidinedione. The solvents which are used are DMF, DMAC, DMSO and NMP, preferably NMP. Generally 2 to 20 volumes, preferably 2.5 to 5 volumes of NMP are used.

Preferred 1-substituted-4-oxocyclic ureas are selected from the group consisting of: 1-[[[5-(4-chlorophenyl)-2-furanyl]methylene]amino]-2,4-imidazolidinedione; 1-[[[5-(4-methanesulfonamidophenyl)-2-furanyl]methylene] amino]-2,4-imidazolidinedione; 1-[[[5-(4-fluorophenyl)-2-furanyl]methylene]amino]-2,4-imidazolidinedione; 1-[[[5-(4-nitrophenyl)-2-oxazolidinyl])methylene]amino]-2,4-imidazolidinedione; 1-[[[5-(4-methylphenyl)-furanyl]methylene]amino]2,4-imidazolidinedione; 1-[[[5-(3,4-dimethoxyphenyl)-2-furanyl]methylene]amino]-2,4-imidazolidinedione. In making Azimilide, the 1-substituted-4-oxocyclic urea which is used is 1-[[[5-(4-chlorophenyl)-2-furanyl]methylene]amino]-2,4-imidazolidinedione.

The second alkylation takes place at temperatures from 50° to 120° C., preferably at about 75° to 95° C. Preferred amines for this step are selected from the group consisting of dimethylamine; diethylamine; N,N-bis-(2-hydroxyethyl) amine; isopropylamine; N-benzyl-N-methylamine; N-(2-hydroxyethyl)-N-methylamine: N-methylpiperazine; morpholine; 4-hydroxypiperidine; N-methyl-N-phenylamine. The amine used to make Azimilide is N-methylpiperazine. Generally 0.8 to 5 equivalents, preferably 1.2 to 3 equivalents of amine per mole of imidazolidinedione are added.

Following the second alkylation the reaction mixture is cooled to generally −10° to 50° C., preferably 5° to 35° C. The co-solvent used to precipitate the salts is either acetone, methanol, ethanol, or mixtures of the above, preferably acetone. Generally 0 to 20 volumes, preferably 6 to 10 volumes are used. The insoluble salts are collected by filtration and washed with co-solvent.

Water is added to the reaction mixture to prepare for salt formation. Generally 0 to 5 volumes, preferably 0.5 to 2.8 volumes of water are used. The acid which is used to form the desired salt is hydrochloric.

Generally pH is controlled in the range of pH 3 to 7, preferably pH 4.5 to 5 for nucleation followed by further addition of acid to pH 0–3 to precipitate said Azimilide which is collected by filtration in 80 to 90% yield.

Azimilide made according to the process of the present invention is useful for the treatment of various medical disorders; such uses include but are not limited to uses as antifibrillatory and antiarrhythmic agents. Those skilled in the art will also recognize that various acids may be added in the final stages of the process to form various salt forms which may facilitate isolation and handling. Other pharmaceutically acceptable salts such as, for example, sulfate and hydrobromide can be prepared according to the process of the present invention and are included in the scope thereof.

This process is illustrated by the following general scheme:

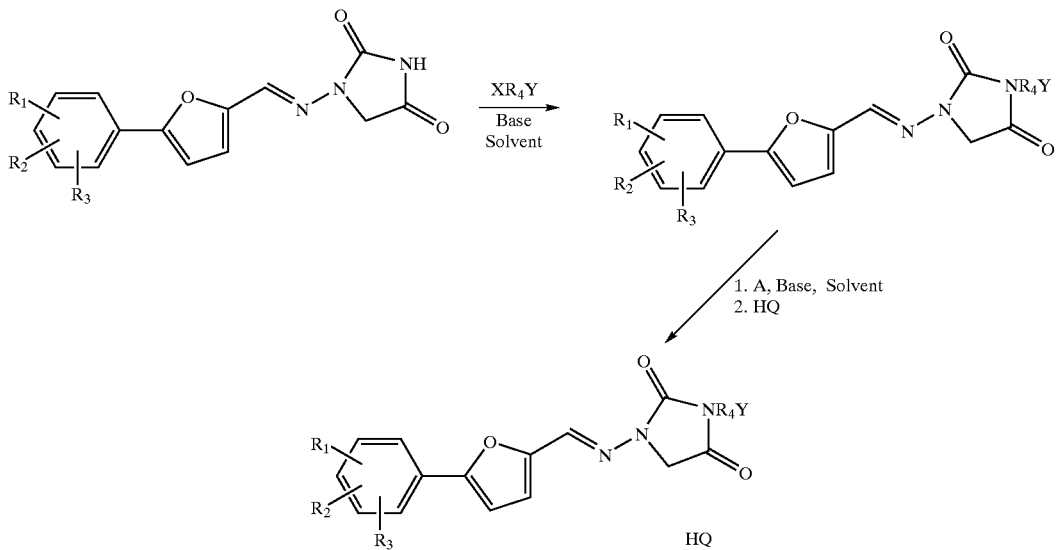

wherein
- $R_1$, $R_2$, and $R_3$ are independently selected from the group consisting of H, Cl, F, Br, $NH_2$, $NO_2$, COOH, $CH_3SO_2NH$, $SO_3H$, OH, alkoxy, alkyl, alkoxycarbonyl, hydroxyalkyl, carboxyalkyl, and acyloxy;
- $R_4$ is selected from the group consisting of a substituted or unsubstituted alkyl, alkenyl, alkynyl, alkylacyl, and heteroalkyl;
- A is a substituted or unsubstituted, saturated or unsaturated, straight-chain or branched alkyl or alkenyl amino group comprised of 1–7 carbon atoms; or A is a substituted or unsubstituted, saturated or unsaturated heterocycle having 5, 6, or 7 members containing at least one nitrogen, and $R_4$ is attached to this nitrogen;
- X and Y are independently a leaving group, preferably different leaving groups;

wherein said 1,3-disubstituted-4-oxocylic urea is made without isolation of intermediates and comprising the steps:
- (Ia) reacting a 1-substituted-4-oxocyclic urea with a carbon chain containing at least two leaving groups in the presence of a mild base and a solvent to form an adduct containing at least one leaving group, and
- (Ib) condensing the adduct with an amine to form a 1,3-disubstituted-4-oxocyclic urea, and
- (II) recovering said 1,3-disubstituted-4-oxocyclic urea.

The following non-limiting examples illustrate the processes of the present invention:

EXAMPLE 1

Use of Dimethylformamide (DMF) as Reaction Solvent for the Preparation of Azimilide A three-neck 12-L flask fitted with a thermometer, mechanical stirrer, heating mantle, reflux condenser and addition funnel is charged with DMF (4.77 L) and heated to 50° C. 1-[[[5-(4-Chlorophenyl)-2-furanyl]methylene]amino]-2,4-imidazolidinedione (597 g) is added and heating is continued. When dissolution is complete, potassium carbonate (276 g) is charged to the flask and heating is continued to 85° C. After 10 minutes, 1-bromo-4-chlorobutane (370 g) is added, and heating is continued to approximately 100° C. After 35 minutes. N-methylpiperazine (465 g) is added, and the mixture is allowed to stir for 1 hour at 100° C. The reaction mixture is cooled to approximately 10° C. and filtered to remove insolubles. The DMF is removed under reduced pressure at 65–68° C. and replaced with absolute ethanol (3.6 L). The mixture is heated to dissolve the free base and filtered to remove insolubles. The product is precipitated from ethanol (6.0 L total) with the addition of 418 g of concentrated hydrochloric acid and then filtered to give 680 g of the compound.

EXAMPLE 2

Use of Methyl Sulfoxide (DMSO) as Reaction Solvent for the Preparation of Azimilide A three-neck 500-mL flask fitted with a thermometer, mechanical stirrer, heating mantle, reflux condenser and addition funnel is charged with DMSO (200 mL) and 1-[[[5-(4-chlorophenyl)-2-furanyl]methylene]amino]-2,4-imidazolidinedione (20 g). Upon dissolution, potassium carbonate (15.5 g) and 1-bromo-4-chlorobutane (13.6 g) are added, and the mixture is heated to 70° C. over 30 minutes. N-methylpiperazine (19.8 g) is added to the mixture over 15 minutes while heating to 90° C. After a total of 2 hours and 15 minutes, the reaction mixture is cooled to approximately 30° C. and, methanol (200 mL) is added. The mixture is cooled to room temperature and filtered to remove insolubles. The filtrate is acidified with concentrated hydrochloric acid to pH 1–2. The mixture is cooled to 15° C. and filtered to give 30.4 g of the compound.

EXAMPLE 3

Use of N,N-dimethylacetamide (DMAC) as Reaction Solvent for the Preparation of Azimilide A three-neck 2-L flask fitted with a thermometer, mechanical stirrer, heating mantle, reflux condenser and addition funnel is charged with DMAC (200 mL), 1-[[[5-(4-chlorophenyl)-2-furanyl]methylene]amino]-2,4-imidazolidinedione(100 g), 1-bromo-4-chlorobutane (59 g), and potassium carbonate (73 g). The mixture is stirred for approximately 100 minutes while heating to 70° C. N-methylpiperazine (59.5 g) is added, and the mixture is stirred for an additional 3 hours with heating to 86° C. The reaction mixture is cooled to 20° C. and acetone (900 mL) is added. The mixture is filtered to remove insolubles. The filtrate is acidified with concentrated hydrochloric acid to pH 1–2, cooled to 15° C., and filtered to give 122.7 g of the compound.

EXAMPLE 4

Use of N-methylpyrrolidone (NMP) as Reaction Solvent for the Preparation of Azimilide A three-neck 5-L flask fined with a thermometer, mechanical stirrer, heating mantle, reflux condenser and addition funnel is charged with NMP (1.2 L), 1-[[[5-(4-chlorophenyl)-2-furanyl]methylene]amino]-2,4-imidazolidinedione (300 g), 1-bromo-4-chlorobutane (187 g), and potassium carbonate (219 g). The mixture is stirred for approximately 1 hour while heating to 70° C. N-methylpiperazine (149 g) is added, and the mixture is stirred for approximately 150 minutes while heating to 90° C. The reaction mixture is cooled to 20° C. and acetone (2.4 L) is added. The mixture is filtered to remove insolubles. Water (0.42 L) is added to the filtrate and, the mixture is heated to 30° to 35° C. The mixture is acidified with concentrated hydrochloric acid to pH 4.5 to 5, seeded with product, stirred for 1 hour, and then further acidified with concentrated hydrochloric acid to pH 0 to 3. The mixture is cooled to 10° C. and filtered to give 382.8 g of the compound.

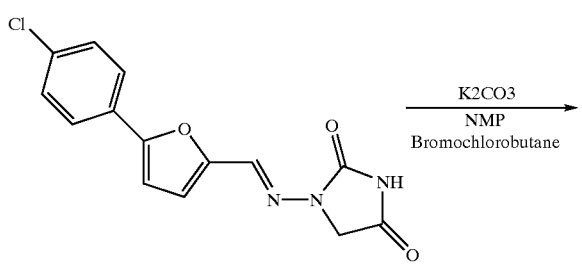

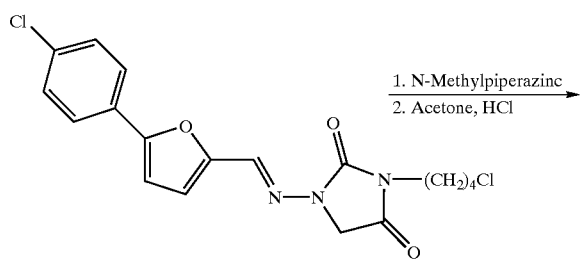

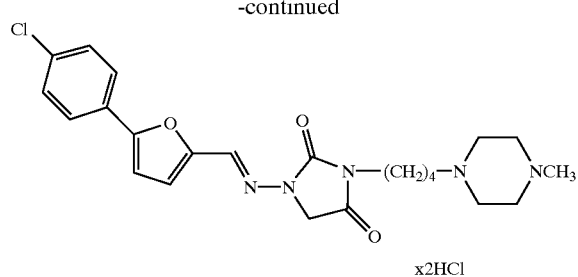

What is claimed is:

1. A process for preparing 1-[[[5-(4-chlorophenyl)-2-furanyl]methylene]amino]-3-[4-(4-methyl-1-piperizinyl)butyl]-2,4-imidazolidinedione having the formula:

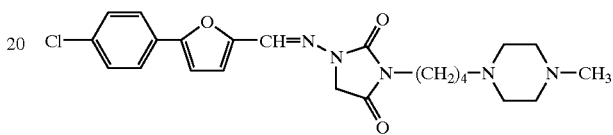

said process comprising the steps of:
   a) reacting 1-[[[5-(4-chlorophenyl)-2-furanyl]methylene]amino]-2,4-imidazolidinedione having the formula:

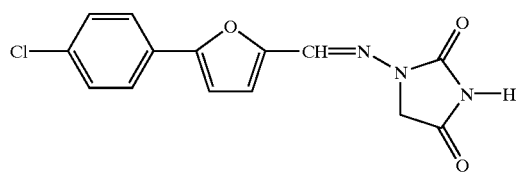

with a carbon chain reagent comprising two leaving groups at the 1 and 4 positions in the presence of a mild base and a polar aprotic solvent to form a 3-N-alkylated 2,4-imidazolidinedione; and b) reacting said crude 3-N-alkylated 2,4-imidazolidinedione with 4-methylpiperizine to form 1-[[[5-(4-chlorophenyl)-2-furanyl]methylene]amino]-3-[4-(4-methyl-1-piperizinyl)butyl]-2,4-imidazolidinedione.

2. A process according to claim 1 wherein said carbon chain reagent is selected from the group consisting of 1-bromo-4-chlorobutane, 1,4-dichlorobutane, 1,4-dibromobutane, and mixtures thereof.

3. A process according to claim 1 wherein said base is selected from the group consisting of N,N-diisopropylethylamine, triethylamine, trimethylamine, 4-dimethylamino pyridine, pyridine, potassium carbonate, sodium carbonate, potassium bicarbonate, sodium bicarbonate, and mixtures thereof.

4. A process according to claim 3 wherein said base is potassium carbonate.

5. A process according to claim 1 wherein said polar aprotic solvent is selected from the group consisting of DMF, DMAC, DMSO, NMP, and mixtures thereof.

6. A process according to claim 1 wherein said base comprises from 0.8 to 4 equivalents of potassium carbonate.

7. A process according to claim 6 wherein said base comprises from 1.2 to 2 equivalents of potassium carbonate.

8. A process according to claim 1 wherein step (a) comprises from 0.8 to 2.5 equivalents of 1-bromo-4-chlorobutane per mole of 1-[[[5-(4-chlorophenyl)-2-furanyl]methylene]amino]-2,4-imidazolidinedione.

9. A process according to claim 8 wherein step (a) comprises from 1 to 1.2 equivalents of 1-bromo-4-chlorobutane per mole of 1-[[[5-(4-chlorophenyl)-2-furanyl]methylene]amino]-2,4-imidazolidinedione.

10. A process according to claim 1 wherein step (a) is conducted at a temperature of from 40° C. to 120° C.

11. A process according to claim 10 wherein step (a) is conducted at a temperature of from 60° C. to 75° C.

12. A process according to claim 1 further comprising the step of isolating 1-[[[5-(4-chlorophenyl)-2-furanyl]methylene]amino]-3-[4-(4-methyl-1-piperizinyl)butyl]-2,4-imidazolidinedione as a hydrochloride salt, said step comprising a first addition of hydrochloric acid until the pH is from 4.5 to 5, a second addition of hydrochloric acid until the pH is from 0 to 3, and collecting a solid hydrochloride salt which forms.

13. A process according to claim 1 further comprising the step of isolating 1-[[[5-(4-chlorophenyl)-2-furanyl]methylene]amino]-3-[4-(4-methyl-1-piperizinyl)butyl]-2,4-imidazolidinedione, said step comprising adding a co-solvent selected from the group consisting of methanol, ethanol, acetone, and mixtures thereof, and collecting a solid which forms.

14. A process for preparing 1-[[[5-(4-chlorophenyl)-2-furanyl]methylene]amino]-3-[4-(4-methyl-1-piperizinyl)butyl]-2,4-imidazolidinedione having the formula:

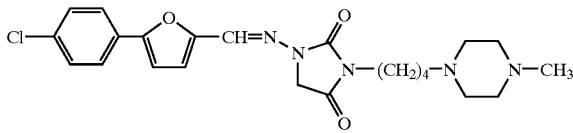

said process comprising the steps of:
a) reacting 1-[[[5-(4-chlorophenyl)-2-furanyl]methylene]amino]-2,4-imidazolidinedione with a carbon chain reagent selected from the group consisting of 1-bromo-4-chlorobutane, 1,4-dichlorobutane, 1,4-dibromobutane, and mixtures thereof, in the presence of a mild base, said base is selected from the group consisting of N,N-diisopropylethylamine, triethylamine, trimethylamine, 4-dimethylamino pyridine, pyridine, potassium carbonate, sodium carbonate, potassium bicarbonate, sodium bicarbonate, and mixtures thereof and an polar aprotic solvent, said polar aprotic solvent is selected from the group consisting of DMF, DMAC, DMSO, NMP, and mixtures thereof, at a temperature of from 40° C. to 120° C. to form a 3-N-alkylated 2,4-imidazolidinedione; and
b) reacting said crude 3-N-alkylated 2,4-imidazolidinedione with 4-methylpiperizine to form 1-[[[5-(4-chlorophenyl)-2-furanyl]methylene]amino]-3-[4-(4-methyl-1-piperizinyl)butyl]-2,4-imidazolidinedione.

15. A process for preparing 1-[[[5-(4-chlorophenyl)-2-furanyl]methylene]amino]-3-[4-(4-methyl-1-piperizinyl)butyl]2,4-imidazolidinedione, said process comprising the steps of:
a) reacting 1-[[[5-(4-chlorophenyl)-2-furanyl]methylene]amino]-2,4-imidazolidinedione having the formula:

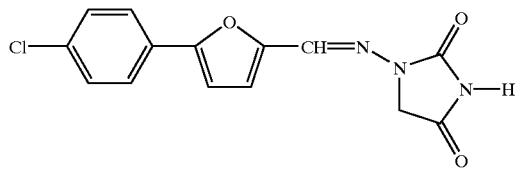

with 1-bromo-4-chlorobutane, in the presence of potassium and a polar aprotic solvent at a temperature of from 40° C. to 120° C. to form a 3-N-alkylated 2,4-imidazolidinedione having the formula:

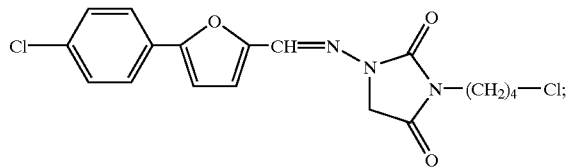

b) reacting said crude 3-N-alkylated 2,4-imidazolidinedione with 4-methylpiperizine to form a 2,4-imidazolidinedione having the formula:

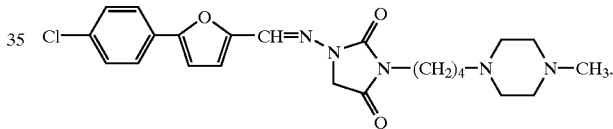

16. A process according to claim 15 further comprising the step of isolating 1-[[[5-(4-chlorophenyl)-2-furanyl]methylene]amino]-3-[4-(4-methyl-1-piperizinyl)butyl]-2,4-imidazolidinedione as a hydrochloride salt, said step comprising a first addition of hydrochloric acid until the pH is from 4.5 to 5, a second addition of hydrochloric acid until the pH is from 0 to 3, and collecting a solid hydrochloride salt which forms.

17. A process according to claim 15 further comprising the step of isolating 1-[[[5-(4-chlorophenyl)-2-furanyl]methylene]amino]-3-[4-(4-methyl-1-piperizinyl)butyl]-2,4-imidazolidinedione, said step comprising adding a co-solvent selected from the group consisting of methanol, ethanol, acetone, and mixtures thereof, and collecting a solid which forms.

* * * * *

UNITED STATES PATENT AND TRADEMARK OFFICE
CERTIFICATE OF CORRECTION

PATENT NO. : 6,414,151 B1  Page 1 of 1
DATED : July 2, 2002
INVENTOR(S) : Patricia Ann Matson et al.

It is certified that error appears in the above-identified patent and that said Letters Patent is hereby corrected as shown below:

Column 4,
Line 14, of the issued patent, delete "tetrahydrofurane" and insert -- tetrahydrofuran --.

Column 7,
Line 46, of the issued patent, delete "K2CO3" and insert -- $K_2CO_3$ --.

Signed and Sealed this

Fourteenth Day of October, 2003

JAMES E. ROGAN
*Director of the United States Patent and Trademark Office*